(12) United States Patent
Klinder et al.

(10) Patent No.: US 10,729,340 B2
(45) Date of Patent: Aug. 4, 2020

(54) SHAPE SENSED ULTRASOUND PROBE FOR FRACTIONAL FLOW RESERVE SIMULATION

(71) Applicant: KONINKLIJKE PHILIPS N.V., Eindhoven (NL)

(72) Inventors: Tobias Klinder, Uelzen (DE); Holger Schmitt, Luetjensee (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1144 days.

(21) Appl. No.: 14/782,605

(22) PCT Filed: Apr. 9, 2014

(86) PCT No.: PCT/IB2014/060559
§ 371 (c)(1),
(2) Date: Oct. 6, 2015

(87) PCT Pub. No.: WO2014/167511
PCT Pub. Date: Oct. 16, 2014

(65) Prior Publication Data
US 2016/0066794 A1   Mar. 10, 2016

Related U.S. Application Data

(60) Provisional application No. 61/811,275, filed on Apr. 12, 2013.

(51) Int. Cl.
*A61B 5/026* (2006.01)
*G16H 40/63* (2018.01)
(Continued)

(52) U.S. Cl.
CPC .......... *A61B 5/026* (2013.01); *A61B 5/02028* (2013.01); *A61B 5/065* (2013.01);
(Continued)

(58) Field of Classification Search
CPC ..... A61B 5/026; A61B 5/02028; A61B 5/065; A61B 5/1076; A61B 5/6852;
(Continued)

(56) References Cited

U.S. PATENT DOCUMENTS 5,830,145 A   11/1998   Tenhoff
6,275,724 B1   8/2001   Dickinson et al.
(Continued)

FOREIGN PATENT DOCUMENTS

CN   101238391 A   8/2008
CN   102598053 A   7/2012
(Continued)

OTHER PUBLICATIONS

Cardoso, F.M. et al., "Realistic IVUS Image Generation in Different Intraluminal Pressures", Ultrasound in Med. & Biol., vol. 38, No. 12, pp. 2104-2119, 2012.

*Primary Examiner* — Peter Luong

(57) ABSTRACT

A medical system includes a medical instrument (102) configured for interventional deployment and a shape sensing system (104) mounted on or in the medical instrument and configured to measure a shape of the medical instrument during the interventional deployment. An imaging device (106) is mounted on or in the medical instrument and configured to image a lumen in which the imaging device is deployed. A registration module (140) is configured to register the shape of the medical instrument to an image of the lumen at a particular time to reconstruct a three-dimensional geometry of the lumen, accounting for motion.

18 Claims, 4 Drawing Sheets

(51) Int. Cl.
| | |
|---|---|
| *A61B 5/02* | (2006.01) |
| *G16H 50/50* | (2018.01) |
| *G16H 30/40* | (2018.01) |
| *A61B 5/06* | (2006.01) |
| *A61B 17/00* | (2006.01) |
| *A61B 90/00* | (2016.01) |
| *A61B 8/12* | (2006.01) |
| *A61B 5/107* | (2006.01) |
| *A61B 5/00* | (2006.01) |
| *A61B 8/08* | (2006.01) |
| *A61B 34/20* | (2016.01) |
| *A61B 34/10* | (2016.01) |
| *A61B 8/00* | (2006.01) |

(52) U.S. Cl.
CPC ............. *G16H 30/40* (2018.01); *G16H 40/63* (2018.01); *G16H 50/50* (2018.01); *A61B 5/0066* (2013.01); *A61B 5/0073* (2013.01); *A61B 5/0084* (2013.01); *A61B 5/066* (2013.01); *A61B 5/1076* (2013.01); *A61B 5/4887* (2013.01); *A61B 5/6852* (2013.01); *A61B 8/085* (2013.01); *A61B 8/0891* (2013.01); *A61B 8/12* (2013.01); *A61B 8/445* (2013.01); *A61B 8/5276* (2013.01); *A61B 2017/00084* (2013.01); *A61B 2034/105* (2016.02); *A61B 2034/2051* (2016.02); *A61B 2034/2061* (2016.02); *A61B 2090/367* (2016.02); *A61B 2090/3735* (2016.02); *A61B 2090/3782* (2016.02); *A61B 2560/0475* (2013.01)

(58) Field of Classification Search
CPC ... A61B 5/4887; A61B 5/0084; A61B 5/0073; A61B 5/0066; A61B 5/066; A61B 2034/2061; A61B 2034/105; A61B 2034/2051; A61B 2560/0475; A61B 2090/3735; A61B 2090/3782; A61B 2017/00084; A61B 8/085; A61B 8/5276; A61B 8/12; A61B 8/0891; A61B 8/445; G16H 40/63; G16H 50/50; G16H 30/40
See application file for complete search history.

(56) References Cited

U.S. PATENT DOCUMENTS

| | | |
|---|---|---|
| 6,612,992 B1 | 9/2003 | Hossack et al. |
| 2005/0288577 A1 | 12/2005 | Weese |
| 2006/0161062 A1 | 7/2006 | Arditt et al. |
| 2011/0071404 A1 | 3/2011 | Elbasiony et al. |
| 2014/0155737 A1 | 6/2014 | Manzke et al. |

FOREIGN PATENT DOCUMENTS

| | | |
|---|---|---|
| CN | 102883655 A | 1/2013 |
| EP | 2538361 A2 | 12/2012 |
| JP | 2003038493 A | 2/2003 |
| JP | 2008526387 A | 7/2008 |
| JP | 2013518656 A | 5/2013 |
| JP | 2014526927 A | 10/2014 |
| WO | 2012073863 A1 | 6/2012 |
| WO | 2012164481 A1 | 12/2012 |
| WO | 2013024418 A | 2/2013 |
| WO | 2013024418 A1 | 2/2013 |
| WO | 2013030764 A1 | 3/2013 |

SHAPE SENSED ULTRASOUND PROBE FOR FRACTIONAL FLOW RESERVE SIMULATION

CROSS-REFERENCE TO PRIOR APPLICATIONS

This application is the U.S. National Phase application under 35 U.S.C. § 371 of International Application Serial No. PCT/IB/2014/060559, filed on Apr. 9, 2014, which claims the benefit of U.S. Application Ser. No. 61/811,275, filed on Apr. 12, 2013. These applications are hereby incorporated by reference herein.

BACKGROUND

Technical Field

This disclosure relates to medical instruments and more particularly to a shape sensing system used with an ultrasound probe to compute fractional flow reserve in medical applications.

Description of the Related Art

Fractional flow reserve (FFR) is a technique used in coronary catheterization to measure pressure differences across a coronary artery stenosis (narrowing, usually due to atherosclerosis) to determine the likelihood that the stenosis impedes oxygen delivery to the heart muscle (myocardial ischemia). During coronary catheterization, a catheter is inserted using a sheath and guidewire. FFR uses a small sensor on the tip of the wire (commonly a transducer) to measure pressure, temperature and flow to determine the exact severity of a lesion. Current clinical practice is to measure the pressure using a pressure wire before and after a potential stenosis. Alternatively, pullback of the pressure wire can be performed, and pressures are recorded along the vessel. While the pressure wire permits measuring the pressure, its insertion may also lead to distortions in the flow pattern thus causing incorrect measurements.

As a non-invasive alternative, fractional flow reserve (FFR) simulation based on volumetric computed tomographic (CT) angiography (CTA) images is becoming increasingly important. However, one critical component for the FFR simulation is accurate knowledge of the underlying vessel geometry on which the simulation is then calculated.

SUMMARY

In accordance with the present principles, a medical system includes a medical instrument configured for interventional deployment and a shape sensing system mounted on or in the medical instrument and configured to measure a shape of the medical instrument during the interventional deployment. An imaging device is mounted on or in the medical instrument and configured to image a lumen in which the imaging device is deployed. A registration module is configured to register the shape of the medical instrument to an image of the lumen at a particular time to reconstruct a three-dimensional geometry of the lumen, accounting for motion.

A medical system for tracking lumen motion for fractional flow reserve (FFR) simulation includes a medical instrument configured for interventional deployment and a shape sensing system mounted on or in the medical instrument and configured to measure a shape of the medical instrument during the interventional deployment. An imaging device is mounted on or in the medical instrument and configured to image a lumen in which the imaging device is deployed. A processor is included, and memory is coupled to the processor. The memory includes a registration module configured to register the shape of the medical instrument to an image of the lumen at a particular time to provide fused data which reconstructs geometry while accounting for motion of the lumen. A FFR simulation module is configured to compute flow characteristics in the lumen based upon the fused data.

A method for tracking lumen motion includes providing a medical instrument with a shape sensing system mounted on or in the medical instrument and a medical imaging device mounted on or in the medical instrument; concurrently measuring an image a lumen using the medical imaging device and a shape of the medical instrument during an interventional deployment; and fusing the shape of the medical instrument to the image of the lumen at corresponding times to reconstruct a three-dimensional geometry of the lumen, accounting for motion.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
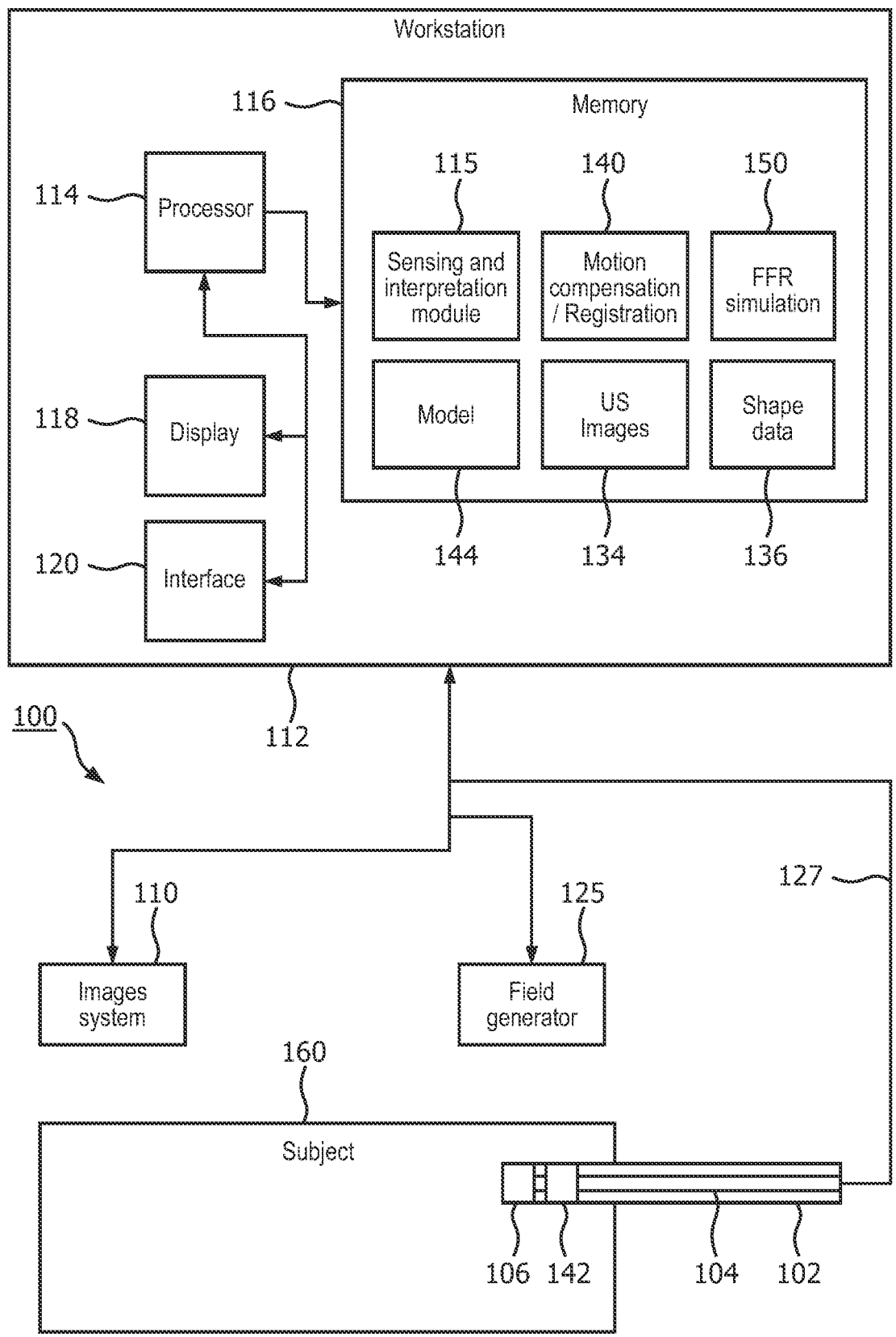
FIG. 1 is a block/flow diagram showing a medical system including a shape sensing system and imaging probe or device in accordance with one embodiment.

Fractional flow reserve (FFR) is a technique used in coronary catheterization to measure pressure differences across, e.g., a coronary artery stenosis. Pressure wires are normally used in an invasive procedure to measure the pressure difference before and after a stenosis, a potential stenosis or area of interest. In accordance with the present principles, an alternative is employed by using a shape sensed imaging probe (e.g., an intravascular ultrasound (IVUS) probe or an optical coherence tomography (OCT) imaging device) for fractional flow reserve simulation. While IVUS (or OCT) collects continuous measurements of lumen diameter and vessel wall, shape sensing permits three-dimensional reconstruction of the vessel even in the presence of a heart beat and respiratory motion. This information can be employed to generate an accurate three or even four-dimensional model (space and time) of the vessel as an input for the FFR calculation using, e.g., computational fluid dynamics.

The shape sensed intravascular ultrasound (IVUS) probe uses a specially designed catheter with a miniaturized ultrasound probe attached to a distal end of the catheter to measure both the lumen and the wall of the blood vessels. While IVUS permits the collection of continuous measurements, reconstruction of the whole vessel geometry is difficult, especially with heart beat and respiratory motions that can cause uncertainty in the location from where the measurements are obtained.

These problems can be overcome by measuring a shape of the IVUS catheter. This can be done by a shape sensing system (e.g., optical shape sensing or electromagnetic tracking of multiple sensors) attached to the IVUS catheter. Knowing both the shape of the IVUS probe as well as the measurements of vessel lumen and wall obtained from the IVUS, the vessel geometry can be reconstructed. Once this information is available, it can be a starting point of a subsequent FFR simulation.

It should be understood that the present invention will be described in terms of medical instruments; however, the teachings of the present invention are much broader and are applicable to any instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk read/write (CD-R/W), Blu-Ray™ and DVD.

Referring now to the drawings in which like numerals represent the same or similar elements and initially to FIG. 1, a system 100 for measuring intraluminal characteristics using shape sensing enabled devices with ultrasound or other imaging systems, and, in particular intravenous ultrasound (IVUS), is illustratively shown in accordance with exemplary embodiments. System 100 may include a workstation or console 112 from which a procedure is supervised and/or managed. Workstation 112 preferably includes one or more processors 114 and memory 116 for storing programs and applications. Memory 116 may store a sensing and interpretation module 115 configured to interpret feedback signals (e.g., electromagnetic or optical) from a shape sensing device or system 104. Sensing and interpretation module 115 is configured to use the optical signal feedback (and any other feedback, e.g., electromagnetic (EM) tracking if EM tracking is employed instead of optical shape sensing) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc. The medical device 102 includes an ultrasonic probe 106 configured to generate and receive ultrasonic waves to image a volume or subject 160 and in particular a vessel wall or geometry. In addition to the instantaneous shape information collected from the US probe 106, an overall shape of the vessel 160 due to movement can be collected using the shape sensing system 104. US probe 106 works in conjunction with an imaging system 110, which may be included in the work station 112 or be employed as a separate unit. Imaging system 110 may include, for example, optical coherence tomography (OCT) for obtaining tissue images instead of US. In such a case, probe 106 can be replaced by a light source and light receiver to carry out OCT. OCT can be considered to effectively be 'optical ultrasound', imaging reflections from within tissue to provide cross-sectional images. OCT is based on light, rather than ultrasound waves. An optical beam is directed at the tissue, and a small portion of this light that reflects from sub-surface features is collected. Interferometry is used to record the optical path length of received photons allowing rejection of most photons that scatter multiple times before detection. OCT can build up clear 3D images of samples by rejecting background signal while collecting light directly reflected from surfaces of interest.

If shape sensing system 104 on device 102 includes optical shape sensing, the shape sensing system 104 includes one or more optical fibers which are coupled to the device 102 in a set pattern or patterns. The optical fibers connect to the workstation 112 through cabling 127 as does the US probe 106 (or OCT device). The cabling 127 may include fiber optics, electrical connections, other instrumentation, etc., as needed.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

In another embodiment, instead of employing optical shape sensing, the shape sensing system 104 may include an array of EM sensors (not shown), which can provide shape sensing capabilities using a field generator 125 and tracking software (e.g., module 115). While only a single shape sensing modality is needed, FIG. 1 shows the structure for both optical and EM tracking shape sensing for illustrative purposes.

Figure 2:
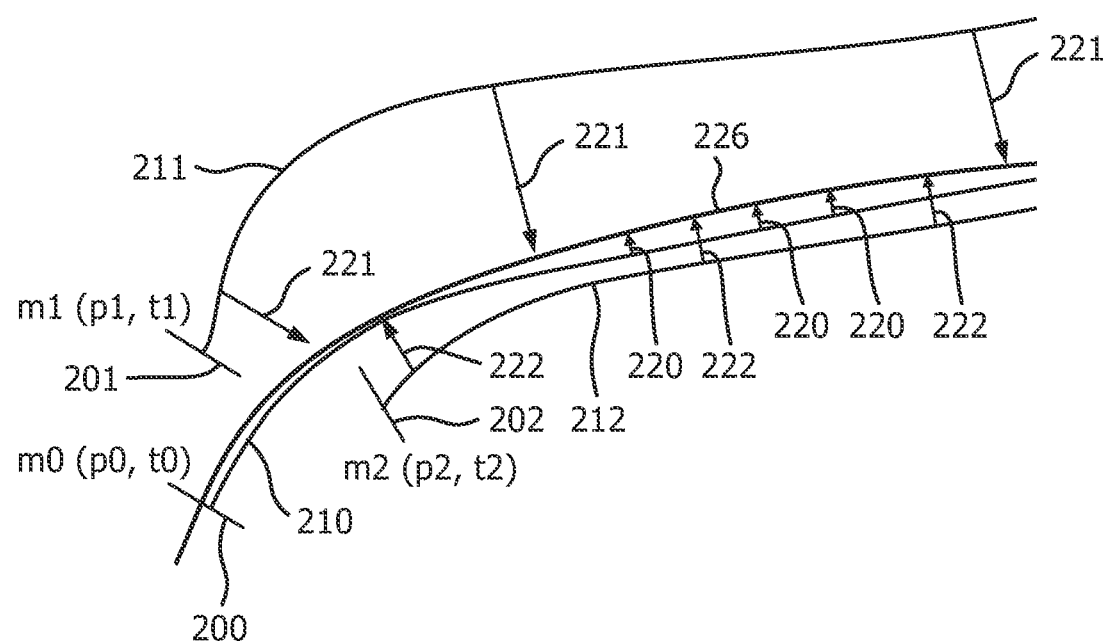
FIG. 2 is a diagram showing shape sensing traces for three time-stamped ultrasonic images and a reference position for computing flow characteristics in accordance with one embodiment.

In one embodiment, workstation 112 includes an image generation module 148 configured to receive feedback from the shape sensing system 104 and display snap-shots or accumulated position data as to where the sensing system 104 has been within the volume 160. For example, for each US measurement $m_x$, a timestamp $t_x$ is associated with an image and position $p_x$ as determined by the US probe 106. The $m_x(p_x, t_x)$ is synchronized and registered with the shape sensing system 104 data to provide the three-dimensional shape of the device 102. The three-dimensional shape of the vessel may instantaneously change due to heartbeat, breathing, patient movement, etc. In accordance with the present principles, the shape data can be employed to correct or account for shape/size changes in the vessel 160 so that a more accurate 3D model can be determined. In one embodiment, the shape data is employed to compare changes between two or more time-stamped images collected by US as shown in FIG. 2. By measuring the shape of the IVUS device 102 (e.g., catheter), the shape of the IVUS probe 106 as well as the measurements of a vessel lumen and wall obtained from the IVUS probe 106 can be employed to reconstruct a more complete vessel geometry. Once this information is available, it can be a starting point for a subsequent fraction flow reserve (FFR) simulation or other computation or study in FFR simulation module 150.

While the insertion of a conventional pressure wire causes local distortions in blood flow, the present embodiments can be employed to simulate the flow based on the acquired accurate 3D vessel model geometry information. IVUS permits collection of continuous measurements, however reconstruction of the whole vessel geometry based on IVUS alone is difficult, especially as heart beat and respiratory motion cause uncertainty in the location from where the measurements are obtained. However, in accordance with the present principles, this problem can be overcome by also measuring the shape of the IVUS catheter. Knowing both, the shape of the IVUS probe as well as the measurements of vessel lumen and wall obtained from the IVUS, the vessel geometry can be reconstructed and stored in a model 144. This applies for OCT as well.

The present embodiments can simulate blood flow based on the acquired geometry information to prevent having to distort the blood flow. With the present embodiments, it is possible to acquire the necessary shape information in an effective manner during an intervention to create a shape model resulting from IVUS and shape measurements. This method has a higher accuracy as compared with a CT scan. Further, vessel wall properties may be determined from the IVUS data and thus, parameters of a vessel model, such as, e.g., the local elasticity, may be modified and integrated into a computational fluid dynamics simulation. A combined IVUS-OSS (optical shape sensing) catheter delivers a fully four-dimensional model 144 of the vessel segment in contrast to the 3D data sets typically derived from CT data sets.

The time dependency of the shape of the blood vessel is extracted from the shape signal in accordance with periodic shape changes due to breathing and cardiac motion. Both breathing and cardiac motion have different cycle lengths and should be easily detectable, and velocity measurements can also give an indication as to when the cardiac or respiratory interval starts. Thus, a cardiac cycle dependent model of the shape can be derived and employed for the cardiac (or respiratory) phase dependent simulation of FFR.

In one embodiment using optical shape sensing, to generate a very accurate model (144), at least two OSS fibers with known spatial relationships at their end points may be included into the IVUS-OSS catheter to solve the rotational registration problem for the measured IVUS data. An estimate of the size (area) of vessel branches branching off a main vessel, through which the catheter is pulled, may be obtained using shape sensing and US with device 102. These branching data may be employed for the calculation of fractional flow reserve data. Branching vessels will appear as "openings" in the vessel wall when performing IVUS pull back. For the FFR simulation tubular structures should be attached to these openings to provide accurate model boundaries.

US images 134 (or other images, e.g., OCT) and shape sensing data (images) 136 can be registered and displayed on a display device 118. Workstation 112 includes the display 118 for viewing internal images of a subject (patient) or volume 160 and may include the images 134 and 136 as an overlay or other rendering of the history of positional changes over time.

A motion compensation and simulation module 140 (or registration module) includes algorithms for three-dimensional vessel geometry registration and compensation using vessel wall information (US) and shape data (shape sensing). The module 140 may be employed to fuse or register measurements both from IVUS and shape sensing and perform 3D modeling for instantaneous geometry measurements to increase the measurement accuracy for applications such as FFR simulation and the like. The module 140 may output the model 144 to better approximate flow in a blood vessel, e.g., for the FFR simulations in module 150.

FFR may also employ other parameters, e.g., pressure, temperature and flow data measured by one or more sensors or transducers 142 to determine the exact severity of the lesion or to gather geometric or other data to build the model 144. These parameters are not needed but may provide additional information in some embodiments. FFR simulations may be performed by the workstation 112, or the collected data may be employed by other systems.

Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

Referring to FIG. 2, US data at three positions ($p_0$, $p_1$, $p_2$), respectively occurring at time instances ($t_0$, $t_1$, $t_2$), are shown as cross-sectional lines 200, 201 and 202. A shape-sensed IVUS provides shapes 210, 211 and 212 going into the cross-sectional lines 200, 201 and 202. Shape sensing permits measurement of the corresponding three-dimensional shape of the IVUS catheter. Due to heart beat and breathing motion, significant shifts can occur. However, as the whole shape is measured, registration to a reference shape 226 is possible from which the vessel geometry can be reconstructed. The reference shape 226 may be computed based on the motion (e.g., extrapolation, interpolation, averaging, determining a static position, determining a position where a longest duration position is during a cycle, etc.) as indicated by arrows 220, 221 and 222.

Figure 3:
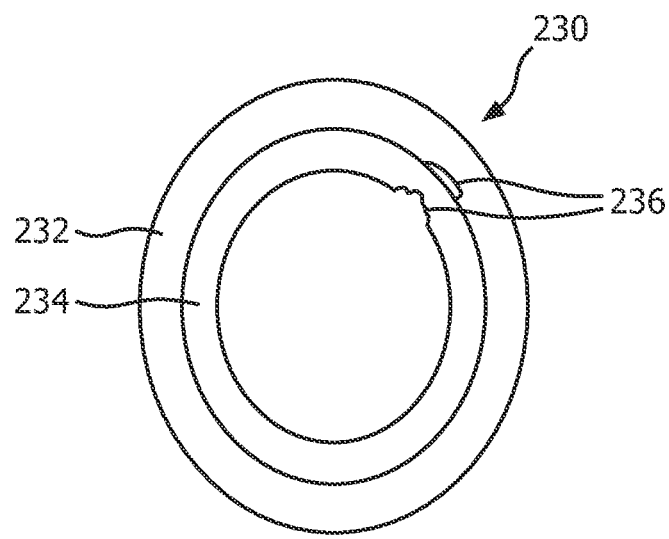
FIG. 3 is an illustration of a cross-section of a blood vessel image gathered by an intravenous ultrasound probe in accordance with one embodiment.

The reference shape 226 can be obtained by first fully inserting the shape sensed IVUS and capturing the shape at one particular time stamp of the US system, e.g., a measurement with a time stamp that is closest to the reference shape. The entire blood vessel can be reconstructed using the reference shape 226 and the US data, which may include a plurality of cross-sectional images 230, one of which is illustratively depicted in FIG. 3. In this way, the movement of a blood vessel 232 is better understood during motion and more accurate computation of FFR or other parameters may be provided. Characteristics affecting blood flow and FFR may include plaque 234 and abnormalities 236, such as, stenosis, etc. will be present in the US images.

FFR is defined as the pressure behind (distal to) a stenosis relative to the pressure before the stenosis. The result is an absolute number; an FFR of 0.50 means that a given stenosis causes a 50% drop in blood pressure. In other words, FFR expresses the maximal flow down a vessel in the presence of a stenosis compared to the maximal flow in the hypothetical absence of the stenosis. During coronary catheterization, a catheter is inserted into the femoral (groin) or radial arteries (wrist). Conventional FFR uses a small sensor on the tip of the device (commonly a transducer) to measure pressure, temperature and flow to determine the exact severity of the lesion. This is done during maximal blood flow (hyperemia), which can be induced by injecting, e.g., adenosine or papaverine. Pressures are recorded across the vessel.

In mathematical terms, FFR is the ratio of maximum blood flow distal to a stenotic lesion to normal maximum flow in the same vessel. FFR=$P_d/P_a$ ($P_d$=pressure distal to the lesion, $P_a$=pressure proximal to the lesion). There is no absolute cut-off point at which FFR becomes abnormal. In clinical trials however, a cut-off point of 0.75 to 0.80 has been employed. Higher values indicate a non-significant stenosis, whereas lower values indicate a significant lesion.

Determining which narrowing or lesion in a blood vessel is affecting a pressure drop is usually difficult. FFR provides a functional evaluation, by measuring the pressure decline caused by a vessel narrowing. By providing three-dimensional shape data in conjunction with US imaging, the shape and dynamics of the blood vessel can be accounted for and better understood to provide better FFR simulation estimates. FFR simulations in accordance with the present principles are able to simulate the flow along the whole vessel without an inserted probe for pressure measurements. This is in contrast with conventional FFR which only takes measurements at two points (before and after the stenosis) with the insertion of a probe for pressure measurements.

Knowing both the shape of the IVUS probe as well as the measurements of vessel lumen and wall obtained from the IVUS, the vessel geometry can be reconstructed. For example, the present system (100, FIG. 1) can measure the shape continuously together with the IVUS probe that provides a lumen measurement of a vessel cross section. The aim is now to combine all the cross section measurements to get the 3D-reconstruction of the vessel geometry. The measurements are collected while inserting the probe (106). If the system were static, one would only need to insert the probe and collect the measurements. However, as breathing motion and heart beat are overlaid, the measurements have to be registered into one common coordinate system. For this registration, the shape information can be beneficial as this allows registration of one centerline onto the other, e.g., reference shape 226, by searching from one centerline for the closest point on the other centerline. Once this information is available, it can be employed for subsequent FFR simulation.

In one example, a shape of the catheter is known at each point in time providing a 3D position and a direction vector. The orientation of the IVUS probe is known as well due to the shape sensing system (e.g., multiple optical fibers). The IVUS measurements are registered to the same coordinate system at the shape of the catheters and the cross-sections of the IVUS are aligned along the shape. The resulting high resolution vessel lumen is represented as a surface model of all the cross-sections and used as an input in FFR calculation.

Figure 4:
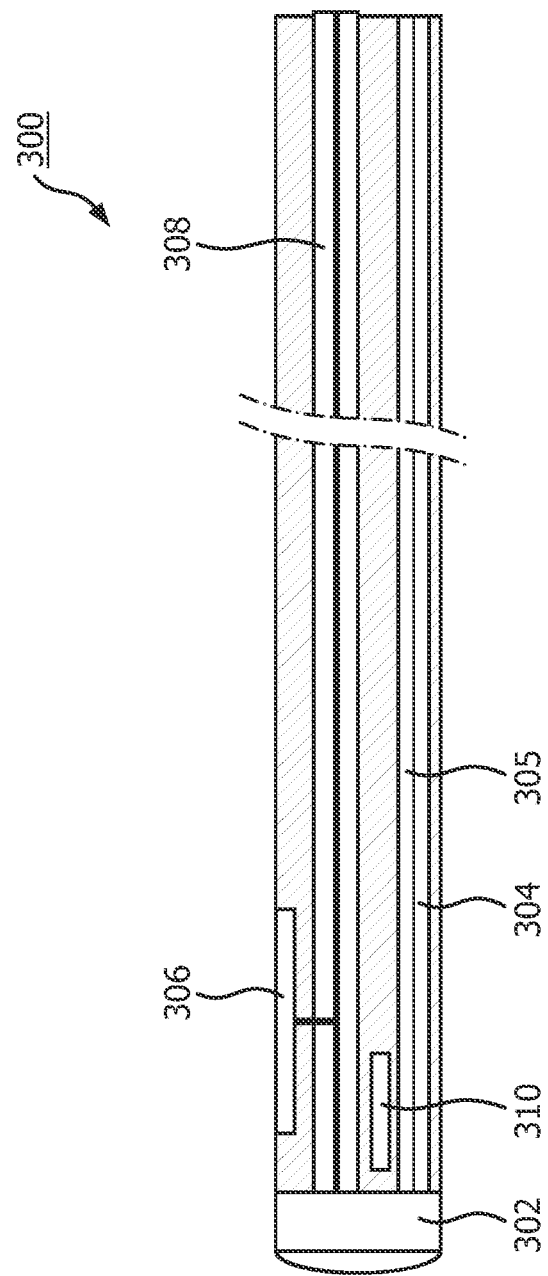
FIG. 4 is a side view of an illustrative medical instrument for performing fractional flow reserve (FFR) measurements in accordance with the present principles.

Referring to FIG. 4, a shape sensed IVUS device 300 is illustratively shown in accordance with one embodiment. The device 300 includes a catheter; however, other medical instruments may be configured to provide the needed functionality for shape sensed imaging for intraluminal blood vessels. The device 300 includes an US probe 302 for IV recording of lumen and vessel wall geometry. The device includes a shape sensing device 304 including, e.g., optical fibers 305 (either with fiber Bragg gratings or with Rayleigh sensing) or multiple electromagnetic sensors.

An optional transducer 306 may be mounted at or near a distal end portion of the device 300 or may be provided through a channel 308 in the device 300 for making pressure and/or temperature readings.

In one embodiment, the shape sensing device 304 may include a single electromagnetic sensor 310 at a tip of the device 300 (e.g., catheter). This simplified embodiment does not to measure the whole shape of the IVUS catheter (300) but only a position of the tip. In this case, the reduction of the shape sensing capabilities needs to be compensated for by a more advanced motion compensation algorithm (in module 140) that restores the three-dimensional shape not by registration to a reference shape but only from the IVUS measurements together with the tip position information as it is moved along the blood vessel. It should be understood that the device 300 may include other features and capabilities instead of or in addition to those described. For example, a scope, a balloon, etc. may be mounted on the device 300 or deployed through the channel 308.

Figure 5:
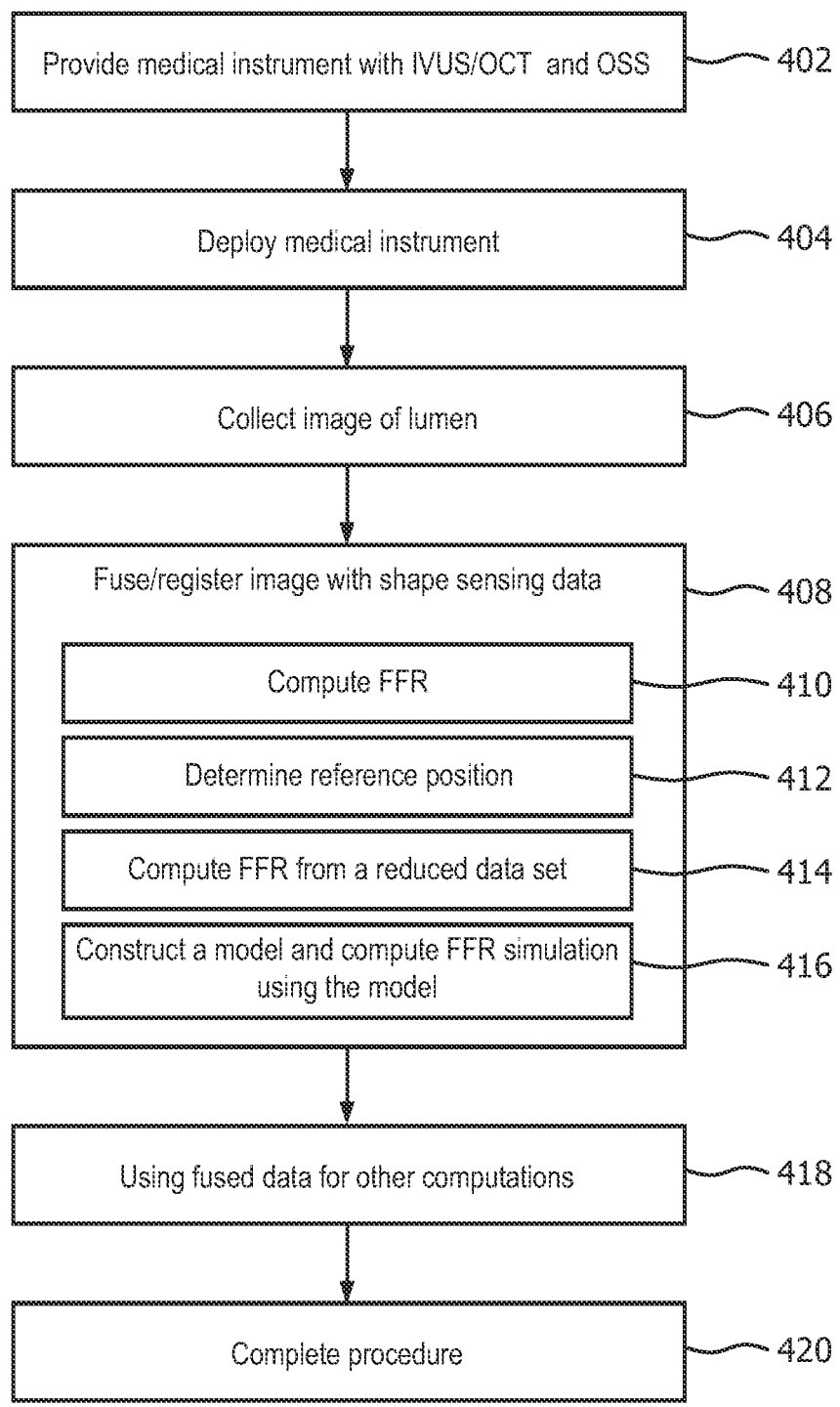
FIG. 5 is a flow diagram showing a method for determining three-dimensional geometry of a lumen in motion in accordance with illustrative embodiments.

Referring to FIG. 5, a method for reconstructing lumen geometry is shown in accordance with the present principles. In block 402, a medical instrument (e.g., a catheter) is provided with a shape sensing system mounted on or in the medical instrument and an ultrasonic probe mounted on or in the medical instrument. In block 404, the medical instrument is intravenously deployed to determine characteristics of a blood vessel or other lumen. In block 406, an image of the lumen is collected using the ultrasonic probe (or OCT device) while concurrently measuring a shape of the medical instrument during the interventional deployment. The shape sensing system may include a fiber optic shape sensing system, which may include two or more fibers, a plurality of serially disposed electromagnetic sensors, or a single electromagnetic sensor at a tip of the medical instrument.

In block 408, the shape of the medical instrument is fused with the image of the lumen at corresponding times to model the geometry of the lumen and account for motion of the lumen during a measurement. In block 410, fractional flow reserve is computed based upon fused data from the shape of the medical instrument and the image of the lumen. In block 412, a reference position between data points in time may be computed to account for motion of a moving lumen. The reference position may be computed based upon surrounding or sequential data from which characteristics can be determined at a given time. The reference position may be determined based on averaging of positions before and after a given time or interpolating or extrapolating the reference position.

In block 414, the fused data may include less than a whole set of shape data for the instrument. This will help to reduce the amount of processed data, resulting in reduced processing time and costs. In block 416, a model of the lumen may be constructed based upon the shape and the image of the lumen. The model may be employed to compute fractional flow reserve across a length of a blood vessel. This may be employed to avoid distortion of the blood flow caused by the presence of the medical instrument in the blood vessel or lumen. In block 418, other computations may be carried out based on the more accurate tracking of the motion of the lumen.

In block 420, the procedure progresses as needed followed by the removal of the medical instrument and closure of the incision from which the instrument enters the body of a subject.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for shape sensed ultrasound probe for fractional flow reserve simulation (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical system, comprising:
a medical instrument configured for interventional deployment;
a shape sensing system mounted on or in the medical instrument and configured to measure a shape of the medical instrument during the interventional deployment;
an imaging device mounted on or in the medical instrument and configured to image a lumen in which the imaging device is deployed concurrently with measuring the shape of the medical instrument; and
a registration module configured to register the measured shape of the medical instrument to an image of the lumen at a particular time to reconstruct a three-dimensional geometry of the lumen, accounting for motion.

2. The system as recited in claim 1, wherein the shape sensing system includes a fiber optic shape sensing system.

3. The system as recited in claim 1, wherein the lumen is a blood vessel and the device is employed to create a model for fractional flow reserve simulation.

4. The system as recited in claim 1, wherein the imaging device includes an ultrasonic probe or a device for optical coherence tomography.

5. The system as recited in claim 1, wherein shape data is collected at a plurality of times and positions to compute a reference position to compute the three-dimensional geometry of the lumen, accounting for motion.

6. The system as recited in claim 1, further comprising a model of the lumen constructed based upon the shape and the image of the lumen.

7. The system as recited in claim 6, wherein the model is employed to compute fractional flow reserve across a length of a blood vessel.

8. The system as recited in claim 1, wherein the shape sensing system includes at least one electromagnetic sensor.

9. A medical system for tracking lumen motion for fractional flow reserve (FFR) simulation, comprising:
a medical instrument configured for interventional deployment;

a shape sensing system mounted on or in the medical instrument and configured to measure a shape of the medical instrument during the interventional deployment;

an imaging device mounted on or in the medical instrument and configured to image a lumen in which the imaging device is deployed concurrently with measuring the shape of the medical instrument;

a processor; and a memory coupled to the processor, the memory including:

a registration module configured to register the shape of the medical instrument to an image of the lumen at a particular time to provide fused data which reconstructs geometry while accounting for motion of the lumen; and a FFR simulation module configured to compute flow characteristics in the lumen based upon the fused data.

10. The system as recited in claim 9, wherein the shape sensing system includes a fiber optic shape sensing system.

11. The system as recited in claim 9, wherein the imaging device includes an ultrasonic probe or a device for optical coherence tomography.

12. The system as recited in claim 9, wherein shape data is collected at a plurality of times and positions to determine a reference position to compute the three-dimensional geometry of a moving lumen.

13. The system as recited in claim 9, further comprising a model of the lumen constructed based upon the shape of the medical instrument and the image of the lumen.

14. The system as recited in claim 13, wherein the model is employed to compute fractional flow reserve across a length of a blood vessel.

15. A method for tracking lumen motion, comprising:

providing a medical instrument with a shape sensing system mounted on or in the medical instrument and a medical imaging device mounted on or in the medical instrument;

concurrently measuring an image of a lumen using the medical imaging device and a shape of the medical instrument during an interventional deployment; and fusing the shape of the medical instrument to the image of the lumen at corresponding times to reconstruct a three-dimensional geometry of the lumen, accounting for motion of the lumen.

16. The method as recited in claim 15, wherein measuring the shape of the medical instrument comprises performing shape sensing using a fiber optic shape sensing system.

17. The method as recited in claim 15, wherein measuring the image of the lumen comprises performing ultrasonic or optical coherence tomography (OCT) imaging.

18. The method as recited in claim 15, further comprising:

constructing a model of the lumen based upon the shape of the medical instrument and the image of the lumen; and computing fractional flow reserve across a length of the lumen using the model.

* * * * *